(12) United States Patent
Richter et al.

(10) Patent No.: US 11,712,305 B2
(45) Date of Patent: Aug. 1, 2023

(54) NAVIGATIONAL ARRAYS AND RELATED METHODS FOR USE WITH A ROBOTIC ARM

(71) Applicant: Medos International Sarl, Le Locle (CH)

(72) Inventors: Joern Richter, Kandern (DE); Felix Aschmann, Basel (CH); Michael Guetlin, Pratteln (CH)

(73) Assignee: Medos International Sarl, Le Locle (CH)

( * ) Notice: Subject to any disclaimer, the term of this patent is extended or adjusted under 35 U.S.C. 154(b) by 658 days.

(21) Appl. No.: 16/784,488

(22) Filed: Feb. 7, 2020

(65) Prior Publication Data
US 2021/0244478 A1 Aug. 12, 2021

(51) Int. Cl.
*A61B 34/20* (2016.01)
*A61B 34/30* (2016.01)

(52) U.S. Cl.
CPC .............. *A61B 34/20* (2016.02); *A61B 34/30* (2016.02); *A61B 2034/2048* (2016.02)

(58) Field of Classification Search
CPC combination set(s) only.
See application file for complete search history.

(56) References Cited

U.S. PATENT DOCUMENTS

| | | | |
|---|---|---|---|
| 2016/0331479 A1 | 11/2016 | Crawford | |
| 2019/0388161 A1* | 12/2019 | Cicchini | ................ A61B 90/11 |
| 2020/0015857 A1 | 1/2020 | Rout et al. | |

FOREIGN PATENT DOCUMENTS

| | | |
|---|---|---|
| WO | 2018/013536 A2 | 1/2018 |
| WO | 2019/130314 A1 | 7/2019 |

* cited by examiner

*Primary Examiner* — Sameh R Boles
(74) *Attorney, Agent, or Firm* — Condo Roccia Koptiw LLP

(57) ABSTRACT

Navigated instrument guide systems and related methods can identify an absolute position of an instrument received within an instrument mount of a robotic arm. A navigation array unit of the guide system can include a main array and a mounted array. The main array can identify a position of the robotic arm and the instrument mount, while the mounted array can identify a depth position of a distal end of an instrument received within the instrument mount. The instrument can be passed through a lumen of the mounted array as the instrument is inserted into the instrument mount. The mounted array can be configured to translate relative to the instrument mount and the main array with distal translation of the instrument. In this manner, a position of the mounted array can identify a depth position of the instrument without a mechanical connection between the mounted array and the instrument.

22 Claims, 15 Drawing Sheets

FIG. 2C
FIG. 2D
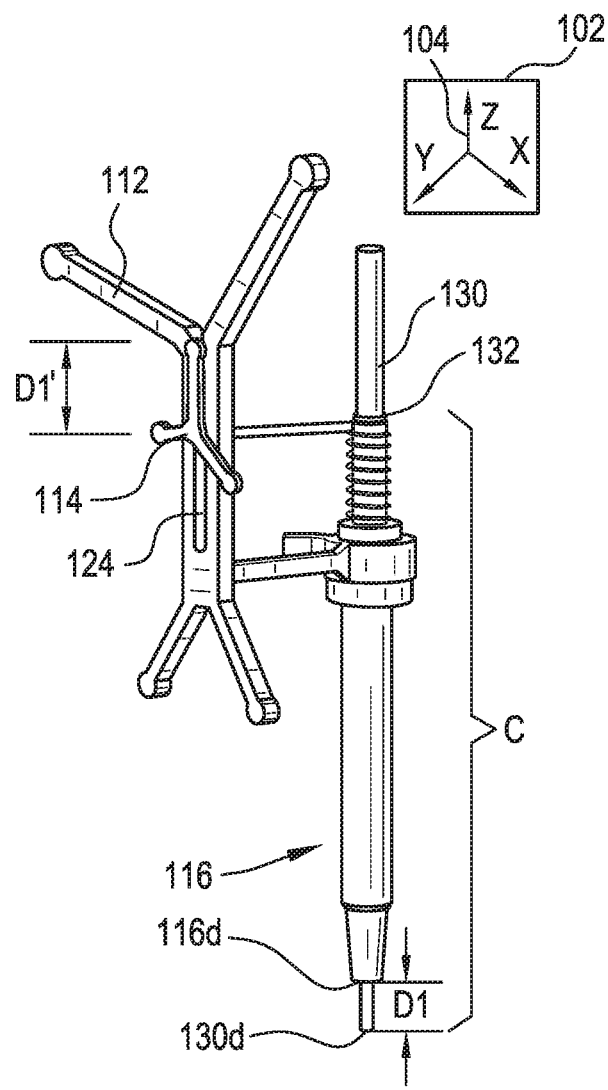
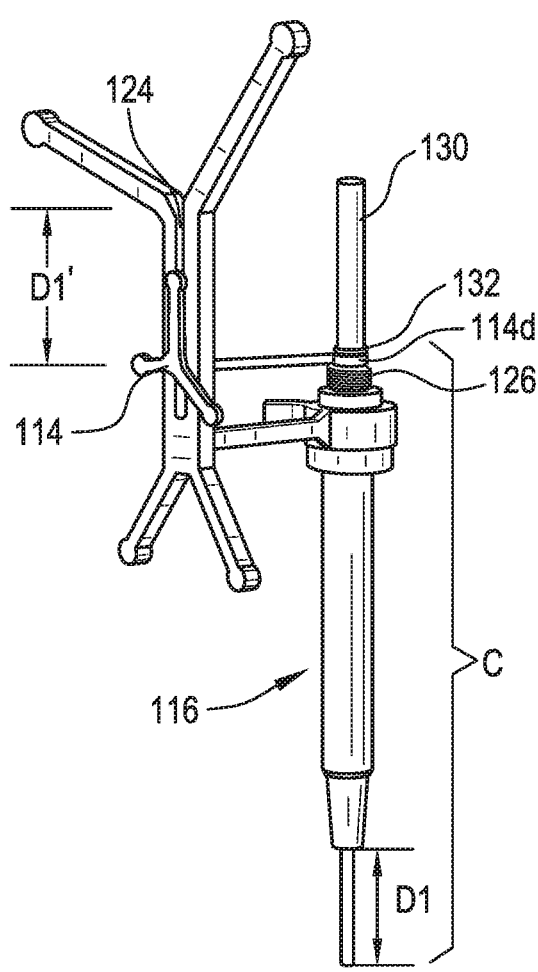

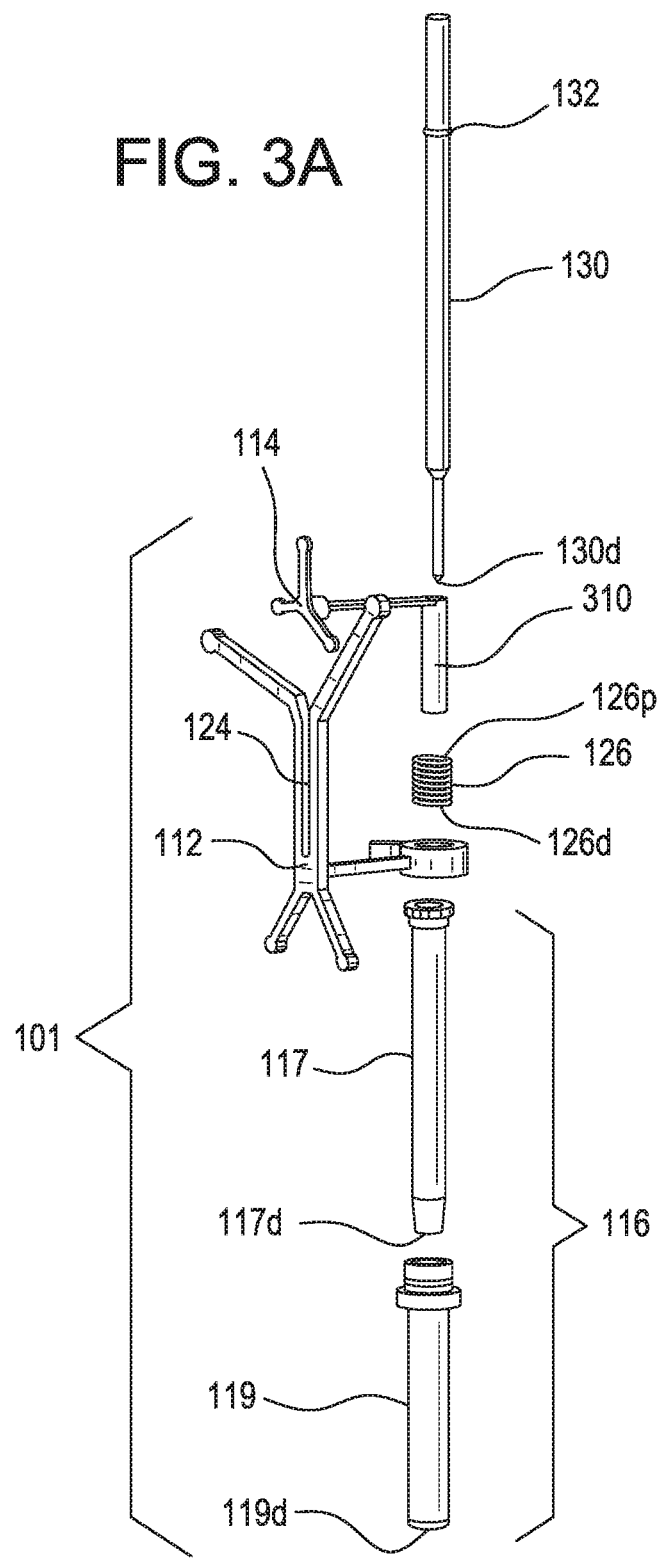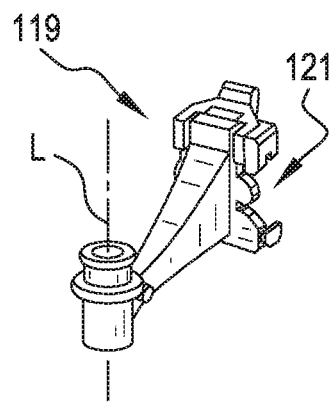

FIG. 8
FIG. 9
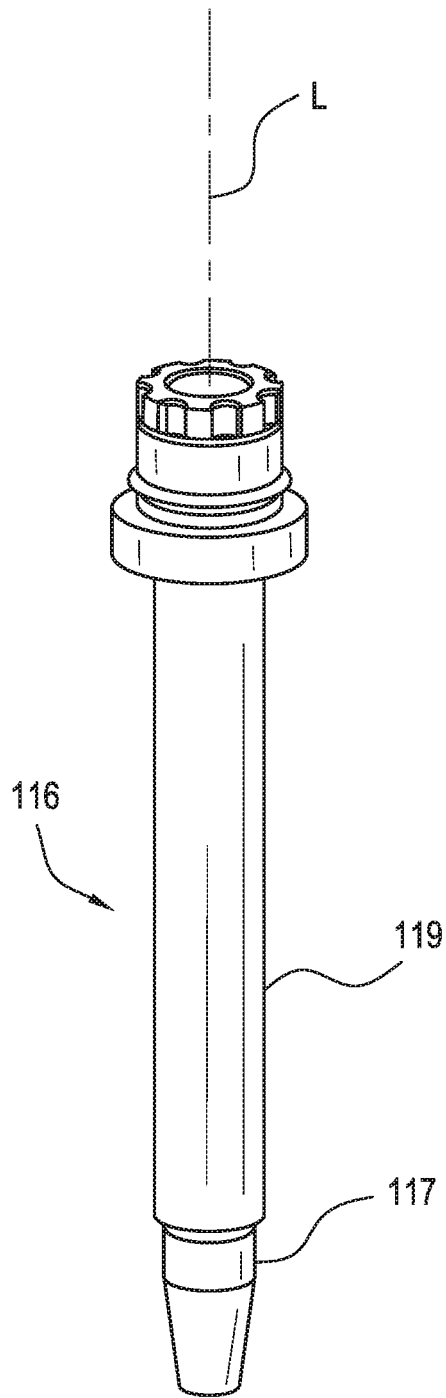
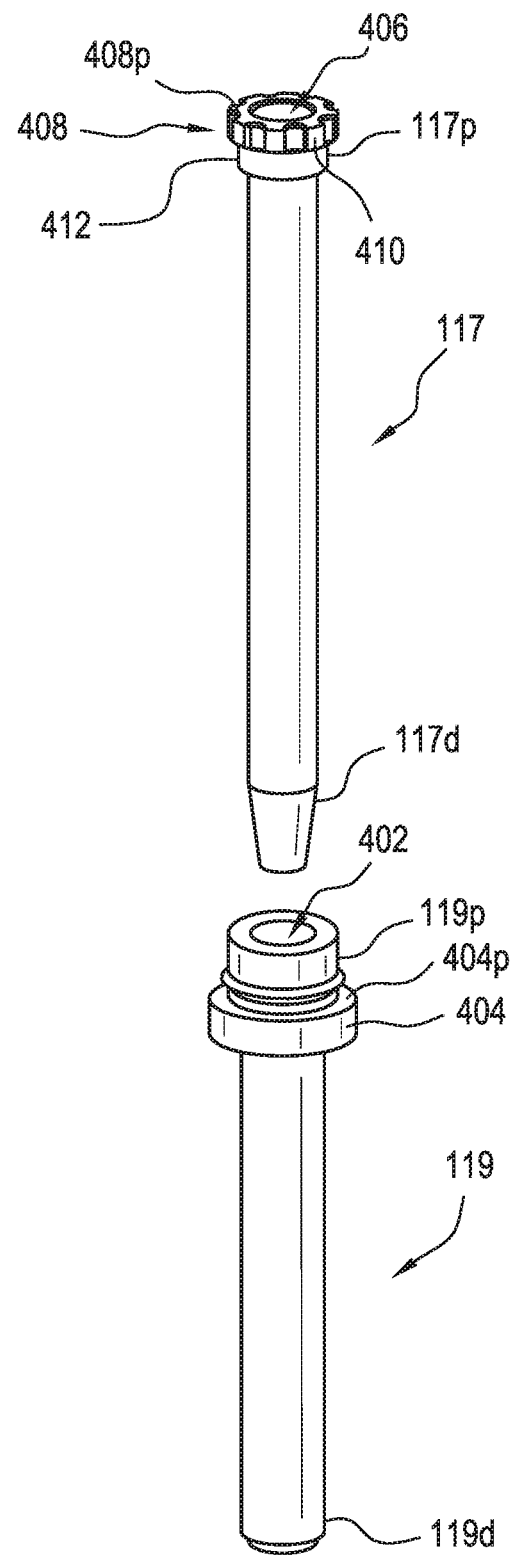

NAVIGATIONAL ARRAYS AND RELATED METHODS FOR USE WITH A ROBOTIC ARM

FIELD

Navigational arrays and related methods are disclosed herein, e.g., for locating, tracking, and/or navigating an instrument in association with a robotic or robot-assisted surgery.

BACKGROUND

Many different surgical procedures utilize some form of surgical navigation or tracking to aid in positioning surgical instruments relative to portions of patient anatomy during a procedure. One such type of procedure is robotic or robot-assisted surgical procedures, where surgical navigation can be important to correctly position a robotically controlled or assisted surgical instrument relative to a patient.

In known surgical navigation technologies, a navigation array or tracker can be mounted on an instrument that is received and/or controlled by a robotic arm to identify a position of the instrument. In some instances, a navigation array or tracker can be formed integrally with the instrument itself. Such solutions, however, can be inconvenient, as the capability to decouple the array from the instrument or to couple the array to other instruments is absent. Further, arrangements having the navigation array integrally-formed with the instrument can require separate instruments for standard and navigation use, thereby raising costs for equipment. In other instances, a navigation array can be removably attached to an instrument and can be used to track a position of multiple instruments over the course of a surgical procedure. This approach, however, requires unmounting and remounting of the array with respect to each particular instrument every time a different instrument is used. These steps can be time consuming, increase the risk of damaging surgical components, such as an instrument, the array, the robotic arm, etc., due to required increased handling of equipment, and can distract and/or disrupt the flow of the surgical procedure. Moreover, in remounting the array onto a new instrument, there can be an increased risk of incorrect calibration.

Accordingly, there is a need for improved systems, methods, and devices for locating a position of an instrument associated with a robotic surgical arm during the course of a robotic or robot-assisted surgical procedure in an accurate, more efficient, and less disruptive manner.

SUMMARY

Navigated instrument guide systems are disclosed herein for accurately and precisely identifying an absolute placement of a robotic arm and an instrument associated with the robotic arm in a manner that does not disrupt a flow of a surgical procedure or require excessive handling of instrumentation. A navigation array unit of an instrument guide system can include a main array configured to locate a distal end of the robotic arm and a mounted array configured to locate a distal tip of an instrument received within the instrument guide system and, more particularly, a depth position of the distal tip of the instrument. In some embodiments, locating the distal end of the robotic arm can include identifying an absolute position of the instrument guide system (e.g., an instrument mount) that can be coupled to the distal end of the robotic arm in a known manner. In other embodiments, locating the distal end of the robotic arm can include identifying a position of a longitudinal axis of the instrument guide system along which an instrument can be received. The main array can be coupled to the distal end of the robotic arm, and the mounted array can be mounted on the main array such that the mounted array can translate relative to the main array. The mounted array can include a lumen through which an instrument can be inserted into an instrument mount of the navigated instrument guide system. The mounted array can move longitudinally relative to the main array and the instrument mount in conjunction with longitudinal movement of the instrument within the instrument mount. Accordingly, movement of the mounted array can be tracked and can identify or locate a depth position of the distal tip of the instrument.

In one aspect, a surgical assembly can include a first array coupled to a surgical robot arm and configured to locate a position of a distal portion of the arm, an instrument mount, and a second array. The instrument mount can be coupled to the robot arm and can have a proximal end, a distal end, and a lumen extending therebetween. The second array can be configured to move relative to the instrument mount and the first array as an instrument is passed through the lumen of the instrument mount and can be configured to move along a path defined by the first array.

The devices and methods described herein can have a number of additional features and/or variations, all of which are within the scope of the present disclosure. In some embodiments, for example, the first array can be configured to locate a position of a longitudinal axis of the instrument mount. The second array can be configured to travel along a slot formed in the first array. In some such embodiments, the second array can also be configured to translate along a longitudinal axis of the instrument mount. The first array can be stationary relative to a distal portion of the robot arm, and the second array can be configured to move longitudinally relative to the first array and the instrument mount with longitudinal movement of an instrument received within the lumen of the instrument mount.

The second array can include an array frame, an extension, and a tubular body. The tubular body of the second array can have a proximal end, a distal end and a lumen extending therebetween. The lumen of the tubular body can be configured to receive an instrument therethrough. In some such embodiments, the lumen of the second array can be coaxial with the lumen of the instrument mount. The second array can include a plurality of tracking elements. In some embodiments, the first array can include a greater number of tracking elements than the second array.

The surgical assembly can further include a biasing element configured to urge the second array proximally relative to the instrument mount. In some embodiments, the biasing element can be disposed within an inner lumen of the instrument mount. In other embodiments, the biasing element can be disposed proximal to the instrument mount.

In another aspect, a surgical robot system can include an instrument mount, an instrument, a first array component, and a second array component. The instrument mount can be coupled to a surgical robot arm, and can have a proximal end, a distal end, and a lumen extending therebetween. The instrument can have an instrument body with a collar formed on the instrument body at a location proximal to a distal tip of the instrument. The first array component can be configured to locate a position of a distal portion of the surgical robot arm. The second array component can have a tubular body received within the lumen of the instrument mount. The second array can be configured to advance distally with the instrument when the collar of the instrument contacts a proximal portion of the second array component.

The surgical robot system can further include a spring extending between the second array component and the instrument mount such that the spring can compress and expand with longitudinally movement of the second array component. In some such embodiments, the spring can be biased away from the instrument mount. The instrument can be any of a drill, tap, needle, stylus, and probe. A distal-facing surface of the collar of the instrument can be configured to contact a proximal-facing surface of the second array component such that distal movement of the instrument can cause distal movement of the second array component. A distance between a proximal end of the second array component and a distal end of the instrument mount can be substantially equal to a distance between the collar formed on the instrument body and the distal tip of the instrument.

In yet another aspect, a surgical method can include positioning an instrument for insertion into a navigated instrument guide, in which the navigated instrument guide can have a main array, a mounted array, and an instrument mount. The method can include inserting the instrument into the navigated instrument guide such that the instrument extends through a lumen of the mounted array and a lumen of the instrument mount, moving the instrument distally through the navigated instrument guide such that the instrument contacts and distally moves the mounted array along a path defined by the main array, and tracking a distal tip of the instrument based on a position of the mounted array.

In some embodiments, the instrument mount can be a distance away from a patient's body. The instrument can include a collar formed thereon that contacts the mounted array and drags the mounted array distally as the instrument is distally advanced through the instrument mount. The mounted array can move distally with respect to the main array and the instrument mount as the instrument is distally advanced through the instrument mount.

Further, in some embodiments, tracking the distal tip of the instrument can be based on the position of the mounted array and a fixed distance between a collar formed on the instrument and a distal tip of the instrument.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF THE DRAWINGS

FIG. 2C illustrates yet another step a method of identifying a depth of an instrument associated with a robotic arm in accordance with the present disclosure;

FIG. 2D illustrates yet another step a method of identifying a depth of an instrument associated with a robotic arm in accordance with the present disclosure;

FIG. 3A shows an exploded view of the navigated instrument guide system shown in FIG. 1;

FIG. 3B shows one embodiment of an adapter of a navigated instrument guide system of the present disclosure;

FIG. 8 is a perspective view of an instrument mount of the navigated instrument guide system shown in FIG. 1;

FIG. 9 is an exploded view of the instrument mount shown in FIG. 8 showing an instrument guide and an adapter;

DETAILED DESCRIPTION

Figure 1:
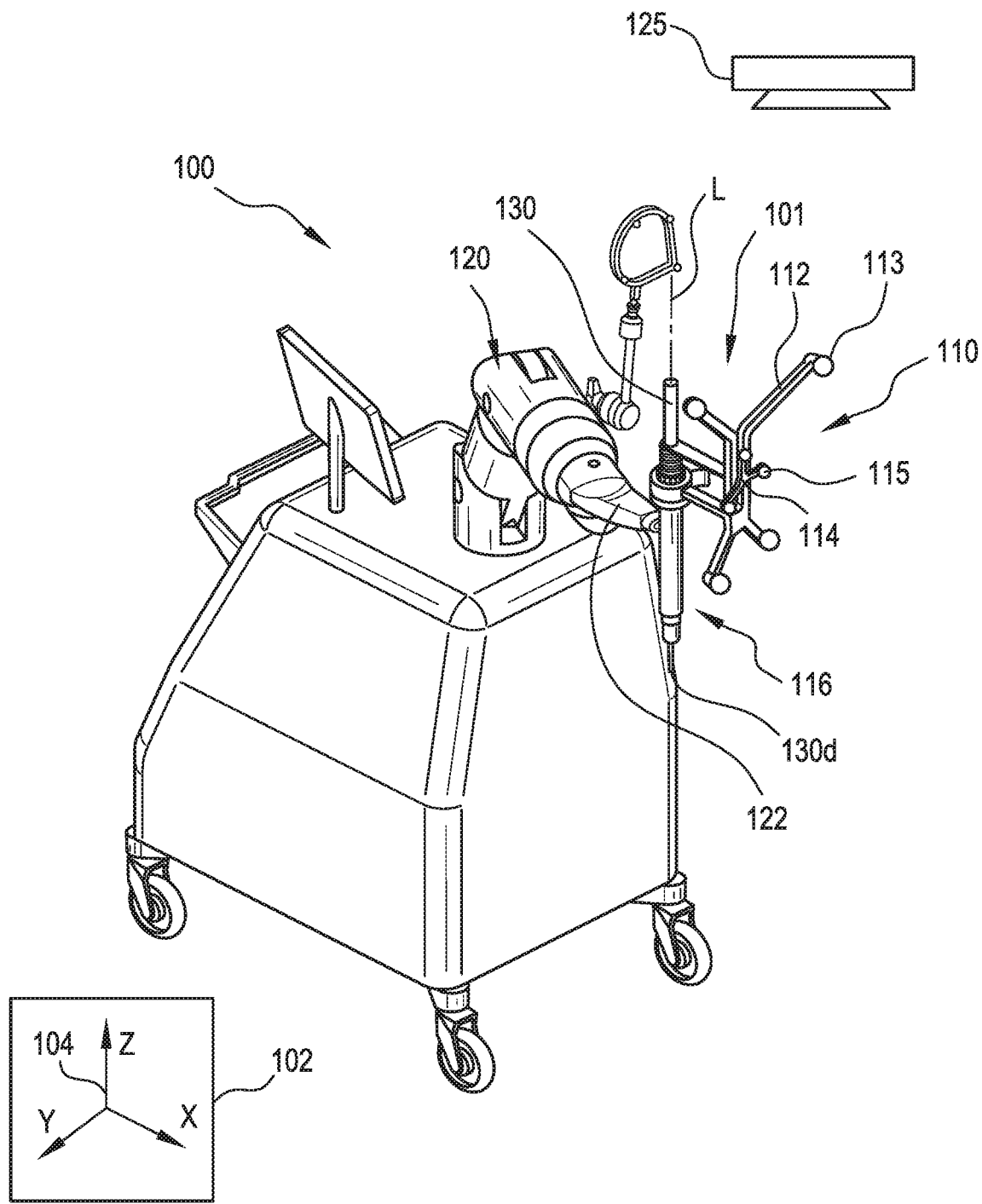
FIG. 1 shows an embodiment of a surgical robotic system including one embodiment of a navigated instrument guide system according to the present disclosure.

Navigated instrument systems and related methods are disclosed herein, e.g., for identifying, visualizing, and/or tracking an absolute placement of a robotic arm and associated instrumentation (i.e., an instrument, device, tool, etc., received at a distal end of the robotic arm configured to interact with the surrounding environment) over the course of a surgical procedure. A navigated instrument system of the present disclosure can include a navigation array unit with a main array (also referred to as a first array) and a mounted array (also referred to as a second array). The navigation array unit can identify a location of a plurality of instruments over the course of the surgical procedure without mechanical attachment between the navigation array unit and any of the plurality of instruments. The main array can be coupled to the surgical robotic arm and can be configured to locate an absolute position of the robotic arm in three-dimensional space. The mounted array can be mounted on the main array and can be configured to locate a position of an instrument received based on a position of the mounted array. More particularly, the mounted array can be configured to receive a portion of an instrument inserted into an instrument mount of the navigated instrument system and can move relative to the main array and the instrument mount with longitudinal movement of the instrument. In this manner, the mounted array can identify and track a depth positioning of a distal end of the instrument without a mechanical connection or fastening between the mounted array and the instrument itself. As such, a need to attach an array to each instrument used throughout a surgical procedure can be eliminated. Accordingly, the navigation arrays of the present disclosure can locate absolute placement of the robotic arm and associated instrumentation during the course of a surgical procedure in an effective and efficient manner without disrupting surgical flow or requiring excessive handling of instrumentation.

Certain exemplary embodiments will now be described to provide an overall understanding of the principles of the structure, function, manufacture, and use of the devices, systems, and methods disclosed herein. One or more examples of these embodiments are illustrated in the accompanying drawings. The devices, systems, and methods specifically described herein and illustrated in the accompanying drawings are non-limiting embodiments. The features illustrated or described in connection with one embodiment may be combined with the features of other embodiments. Such modifications and variations are intended to be included within the scope of the present disclosure.

Additionally, to the extent that linear or circular dimensions are used in the description of the disclosed devices and methods, such dimensions are not intended to limit the types of shapes that can be used in conjunction with such devices and methods. Equivalents to such linear and circular dimensions can be determined for different geometric shapes. Further, in the present disclosure, like-numbered components of the embodiments generally have similar features. Still further, sizes and shapes of the devices, and the components thereof, can depend at least on the anatomy of the subject in which the devices will be used, the size and shape of objects with which the devices will be used, and the methods and procedures in which the devices will be used.

FIG. 1 illustrates an embodiment of a robotic surgical system 100 including one embodiment of a navigated instrument system 101 of the present disclosure coupled to a surgical robotic arm 120. The navigated instrument system 101 can include a navigation array unit 110 and an instrument mount 116. The navigation array unit 110 and the instrument mount 116 can be configured to receive an instrument 130 therein, and can identify a positioning of the instrument 130 and the robotic arm 120 in absolute space (i.e., can identify or locate a position of the instrument 130 and the robotic arm 120 with respect to all degrees of freedom of a three-dimension coordinate system, such as the coordinate system 102 shown in FIG. 1). Identifying the position of the instrument 130 and the robotic arm 120 can include identifying a depth position of the instrument 130. As used herein, the term "depth" can refer to a position along an axis that runs parallel to a longitudinal axis of the instrument mount 116. In the coordinate system 102 shown in FIG. 1, a depth position can refer to a position along a z-axis 104. The navigation array unit 110 can include a main array 112 and a mounted array 114. The main array 112 can identify a position of a distal end 122 of the robotic arm 120. In some embodiments, identifying the position of the distal end 122 of the robotic arm 120 can include identifying an absolute position of the instrument mount 116 that can be coupled to the distal end of the robotic arm 120 in a known manner. In other embodiments, identifying the position of the distal end 122 of the robotic arm 120 can include identifying a position of a longitudinal axis L of the instrument mount 116. For example, as shown in FIG. 1, the longitudinal axis L extends parallel to the illustrated Z-axis. Identifying the position of the longitudinal axis L can include locating a position of the longitudinal axis along the x- and y- axes. The mounted array 114 can identify a depth positioning of the instrument 130 received within the instrument mount 116. In this manner, the navigation array unit 110 can provide complete positioning information to a user (e.g., a surgical robot system, surgeons, nurses, practitioners, etc.) by identifying an absolute position of the robotic arm 120 and the depth position of the instrument 130 associated therewith.

To that end, the main array 112 and the mounted array 114 can include one or more markers 113 and 115, respectively. A navigation system camera 125 can capture a location of the one or more markers 113 and 115. The main array 112 can be coupled with a known and precise relationship to a distal end 122 of the robotic arm 120. In some embodiments, as discussed in detail below, the main array 112 can be coupled to the instrument mount 116 which, in turn, can be coupled to the distal end 122 of the robotic arm 120. The main array 112 can be coupled to the distal end 122 of the robotic arm such that relative movement between the main array and the distal end of the robotic arm is restricted. In other words, the main array 112 can be stationary relative to the distal end 122 of the robotic arm. The location information captured from the markers 113 of the main array can thus identify a location of the robotic arm in three-dimensional space given the known and precise relationship between the distal end 122 of the robotic arm 120 and the main array 112.

The mounted array 114 can be configured to locate the depth of a distal tip 130d of the instrument 130 when the instrument 130 is received within the instrument mount 116. The mounted array 114 can be configured to identify the depth position of the instrument 130 without being mechanically connected or fastened to the instrument 130. As described in detail below, the instrument 130 can pass through a lumen of the mounted array 114 and can drag or move the mounted array 114 distally with distal translation of the instrument. The mounted array 114 and the markers 115 can move absolutely and linearly with translation of the instrument 130. Accordingly, a position and/or movement of the mounted array 114, as captured by the markers 115 and the navigation system camera 125, can identify and track the depth position of the instrument 130.

Figure 2A:
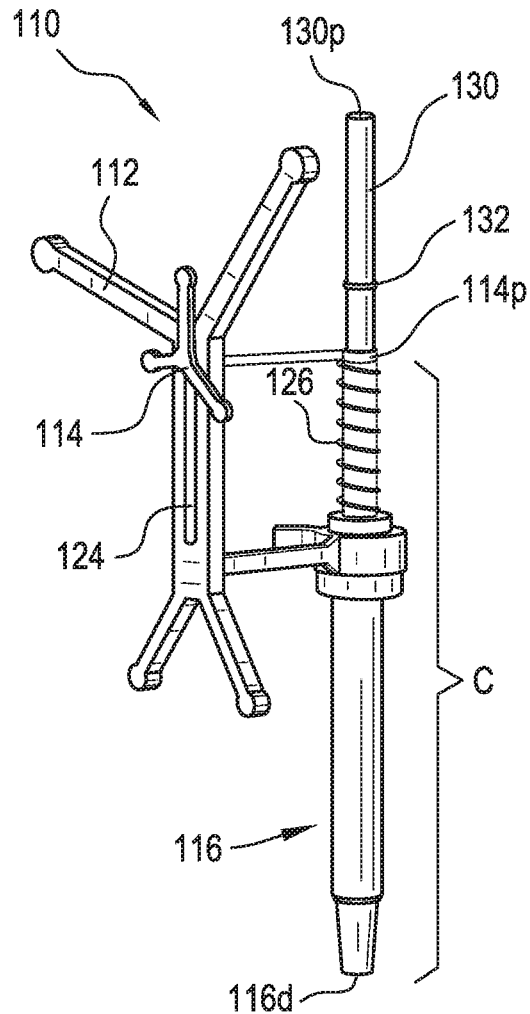
FIG. 2A illustrates a step in an embodiment of a method of identifying a depth of an instrument associated with a robotic arm in accordance with the present disclosure.

FIGS. 2A-2D illustrate an exemplary method of using the navigation array unit 110 to identify an absolute placement of the instrument 130 associated with the robotic surgical arm 120. In FIG. 2A, the instrument 130 can be inserted into the instrument mount 116. The instrument 130 can have an instrument body with a proximal end 130p and a distal end (not visible in FIG. 2A) and a collar 132 formed thereon. The instrument 130 can be inserted such that the distal end of the instrument can be located within a lumen of the instrument guide 116 without extending beyond a distal end 116d of the instrument guide and the collar 132 of the instrument 130 can be positioned proximal to the mounted array 114. More particularly, the collar 132 can be proximal to a proximal end 114p of the mounted array 114. A known length C can define a distance between the proximal end 114p of the mounted array 114 and a distal end 116d of the instrument mount 116. In the insertion position of FIG. 2A (i.e., with the collar 132 of the instrument 130 proximal to the proximal end 114p of the mounted array 114), the mounted array 114 can be located in a first proximal-most position relative to the main array 112. In this proximal-most position, the mounted array 114 can be located at a proximal end of a slot 124 of the main array 112. The mounted array 114 can be configured to translate longitudinally along a path defined by the slot 124 of the main array 112. In some embodiments, the slot 124 can provide structural integrity to the mounted array 114 through contact or tight tolerancing between the mounted array and the main array 112 as the mounted array translates along a path defined by the slot 124. A biasing element 126 can extend in an uncompressed position between the mounted array 114 to the instrument mount 116 and can bias the mounted array proximally relative to the instrument mount.

Figure 2B:
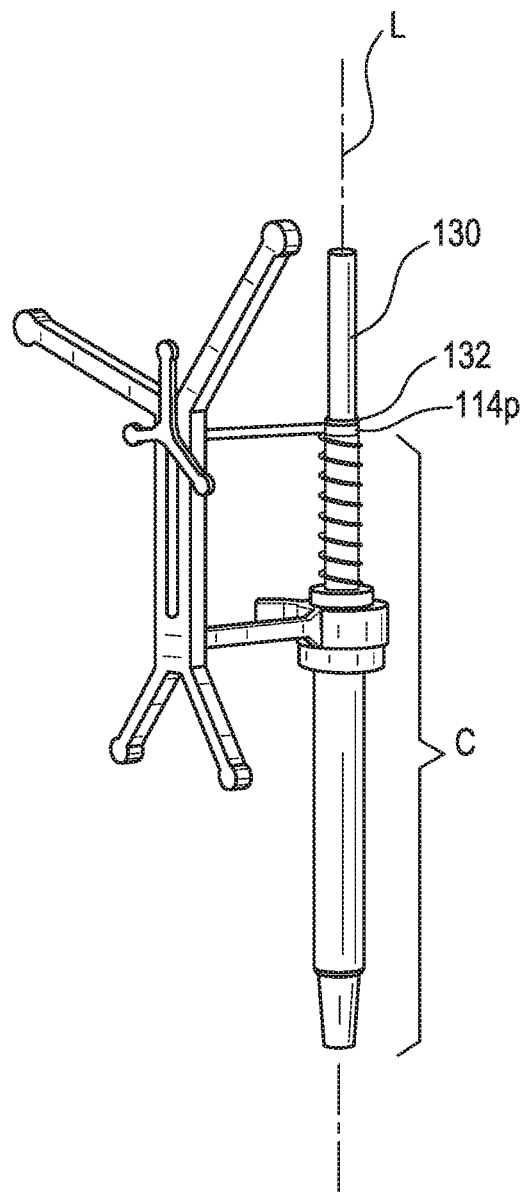
FIG. 2B illustrates another step in an embodiment of a method of identifying a depth of an instrument associated with a robotic arm in accordance with the present disclosure.

As shown in FIG. 2B, the instrument 130 can be moved distally to advance the instrument within the instrument mount 116 to a point when the collar 132 of the instrument contacts the proximal end 114p of the mounted array 114. More particularly, a distal-facing surface of the collar 132 can contact a proximal-facing surface of the proximal end 114p of the mounted array 114. In this configuration (i.e., a point at which the collar 132 of the instrument 130 first contacts the proximal end 114p of the mounted array 114), the mounted array 114 can maintain the proximal-most position of FIG. 2A. As described below, a distance D between the collar 132 of the instrument 130 and a distal end of the instrument 130 can be substantially equal to the distance C between the proximal end 114p of the mounted array 114 and the distal end 116d of the instrument mount 116. Accordingly, in the configuration illustrated in FIG. 2B, the distal end of the instrument 130 and the distal end 116d of the instrument mount 116 can be aligned, and the distance C can represent the distance between the collar 132 to the distal end of the instrument 130. In other embodiments, there can be an additional known setback or buffer distance between the distal end 116d of the instrument mount 116 and the distal end of the instrument 130, such that the distal tip of the instrument is proximal of the distal end 116d by the setback or buffer amount when in the position of FIG. 2B. Because this setback or buffer distance is known, it can be accounted for in determining the position of the distal end of the instrument 130.

As shown in FIG. 2C, with the collar 132 of the instrument 130 in contact with the proximal end 114p of the mounted array 114, the instrument can be distally advanced further within the instrument mount 116 such that the distal end 130d of the instrument can extend distally beyond the distal end 116d of the instrument mount 116. As the instrument 130 moves distally beyond the position at which the collar 132 can contact the proximal end 114p of the mounted array 114 (i.e., the position of FIG. 2B), distal movement of the collar 132 can drag or move the mounted array 114 distally. As the mounted array 114 is dragged distally, the mounted array can translate distally along a path defined by the slot 124 of the main array 112. Accordingly, the mounted array 114 can move in a linear manner with distal movement of the instrument 130. The biasing element 126 can be compressed distally towards the instrument mount 116 by a distal force of the collar 132 as the instrument 130 moves distally. The biasing element 126 can impart a desired drag force that can semi-rigidly maintain a position of the mounted array 114 in the proximal-most position relative to the instrument mount 116 and main array 112, while continuing to permit longitudinal movement of the mounted array if, for example, a user (i.e., a robot or a human) overcomes the drag force with distal translation of the instrument 130 when the collar 132 of the instrument contacts the mounted array. In some embodiments, the desired drag force imparted by the biasing element 126 can aid in seating a drill or other instrument 130 against the instrument mount 116.

The distal end 130d of the instrument can extend a distance D1 beyond the distal end 116d of the instrument mount 116. The distance D1 can be equal to a distance D1' traveled by the mounted array 114 as the mounted array is dragged along the axis of the instrument mount 116 (i.e., the z-axis 104) by the instrument 130. The distance D1' traveled by the mounted array 114 can be determined by tracking of the one or more markers 115 (see FIG. 1) of the mounted array. For example, the navigation system camera 124 (see FIG. 1) can track the markers 115 and calculate the distance D1' traveled by the mounted array 114. As the distance between the proximal end 114p of the mounted array 114 and the distal tip 130d of the instrument remains constant once the collar 132 contacts the proximal end of the mounted array, the distance D1' traveled by the mounted array 114 can be used to identify the depth position of the distal end of the instrument 130. Further, in embodiments in which a known setback or buffer is employed, the distance D1' traveled by the mounted array 114 can be equated to the distance D1 that the distal end of the instrument 130 extends from the instrument mount 116 by subtracting the known setback or buffer from the distance D1' traveled by the mounted array.

FIG. 2D illustrates the instrument 130 in a fully inserted position within the instrument mount 116. In this position, the biasing member 126 can be fully compressed such that further distal translation of the instrument 130 relative to the instrument mount 116 is not possible. The distance D1 that the distal end 130d of the instrument 130 extends beyond the distal end 116d of the instrument mount 116 can be greater than that shown in FIG. 2C. The mounted array 114 can continue to be dragged distally with distal movement of the collar 132 of the instrument 130 such that the distance D1' in the fully inserted position, and, accordingly, a depth position of the distal end 130d of the instrument, can be determined by the mounted array 114. The mounted array 114 can be in a distal-most position within the slot 124 of the main array 112 when the instrument 130 is fully inserted within the instrument mount 116. In some embodiments, the depth of the instrument 130 can be identified when the distal tip 130d of the instrument 130 is located a distance away (i.e., not in contact with) a work surface or a surgical site.

The navigated instrument system 101, as shown in FIG. 1, will now be described in greater detail with reference to FIGS. 3A, 3B, and 4. FIG. 3A illustrates an exploded view of the navigated instrument system 101 and the instrument 130 configured to be received therein. Visible in this figure is the main array 112, the mounted array 114, the biasing element 126, the instrument mount 116, and the instrument 130. In some embodiments, the instrument mount 116 can include an instrument guide 117 and an adapter 119. The instrument guide 117 can be configured to be received within a lumen of the adapter 119 such that a distal end 117d of the instrument guide extends beyond a distal end 119d of the adapter 119. In other embodiments, the instrument mount 116 can be a single tubular member.

The instrument mount 116 can be configured to securely couple to the robotic arm 120 (see FIG. 1) and can be configured to receive an instrument therethrough. More particularly, in some embodiments, the adapter 119 can be securely attached to the robotic arm 120. By way of non-limiting example, FIG. 3B shows an embodiment of the adapter 119 that can be attached to the distal end of the robotic arm 120 with a connection feature 121. Other configurations of the adapter 119 are within the scope of the present disclosure, so long as the adapter 119 can be configured to receive a surgical instrument therein and can maintain a secure and precise connection to the robotic arm 120. In some embodiments, the instrument mount 116 can be slidably received within the adapter 119 such that the instrument mount can slide or translate relative to a longitudinal axis L of the adapter 119. In such embodiments, the instrument mount can be adjusted to a desired positioning along the longitudinal axis L and can be securely locked such that the instrument mount can be maintained in a secure and known position relative to the robotic arm 120.

The main array 112 can be coupled to the instrument mount 116 in a known and precise manner, such that the main array 112 can be used to identify and track a position of the instrument mount 116 and thus, the distal end of the robotic arm 120. The mounted array 114 can be configured such that a portion 312 of the mounted array can be slidably received within the slot 124 of the main array 112, while another portion 310 of the mounted array can be slidably received within a lumen of the instrument mount 116. In the illustrated embodiment, the portion 310 of the mounted array 114 can be slidably received within a lumen of the instrument guide 117. As described in detail below, the mounted array 114 can be slidably received within the main array 112 such that a frame of the mounted array can be in a plane parallel to a plane of a frame of the main array. In use, the main array 112 and the mounted array 114 can be positioned such that both arrays face the navigation camera 125 and do not obstruct surgeon access to a working area.

The biasing element 126, which can be, e.g., a coil or other compression spring, can have a proximal end 126*p* configured to abut a surface of the mounted array 114 and a distal end 126*d* configured to abut a surface of the instrument mount 116. As discussed above, the biasing element 126 can impart a desired drag force that can semi-rigidly maintain a position of the mounted array 114 in a proximal position relative to the instrument mount 116 and main array 112, while continuing to permit longitudinal movement of the drag array if, for example, a user (i.e., a robot or a human) overcomes the drag force with distal translation of the instrument 130 when the collar 132 of the instrument contacts the mounted array. In the illustrated embodiment, the distal end 126*d* of the biasing element 126 can be configured to abut a surface of the instrument guide 117.

Also visible in FIG. 3A is the instrument 130 configured to be received within the instrument mount 116 during a surgical procedure. The instrument 130 can be inserted into a lumen of the mounted array 114 and can extend distally through the lumen of the instrument guide 117 such that the distal end 130*d* of the instrument can extend beyond the distal end of the instrument mount 116. As will be apparent from the assembled navigated instrument system 101, described in detail with respect to FIG. 4 below, in some embodiments, the distal end 116*d* of the instrument mount 116 can be the distal end 117*d* of the instrument guide 117.

Figure 4:
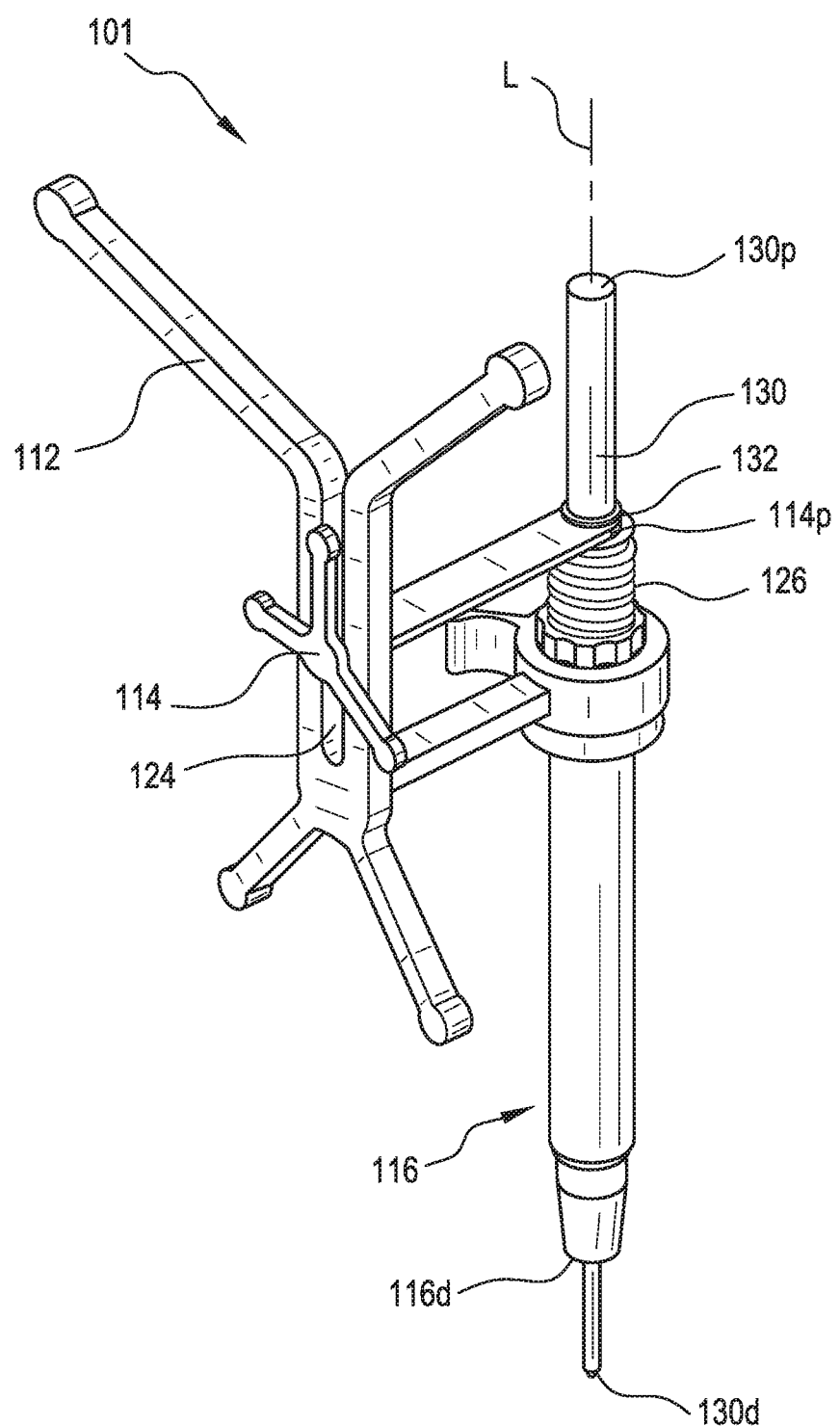
FIG. 4 is a perspective view of the navigated instrument guide system shown in FIG. 1 with an instrument received therein.

Turning now to FIG. 4, the navigated instrument end effector 101 is shown in its assembled configuration with the instrument 130 received therein. The main array 112 can be securely coupled to the instrument mount 116. The mounted array 114 can be received within the slot 124 of the main array 112 and the instrument mount 116 such that the mounted array 114 can translate longitudinally with respect to the main array and the instrument mount with translation of the instrument 130. As shown in FIG. 4, the biasing element 126 can be in an at least partially compressed state between the proximal end 114*p* of the mounted array 114 and a proximal facing surface of the instrument mount 116. The instrument 130 can be received within the instrument mount 116 such that the collar 132 abuts the proximal end 114*p* of the mounted array and can be configured to drag or distally move the mounted array 114.

Figure 5:
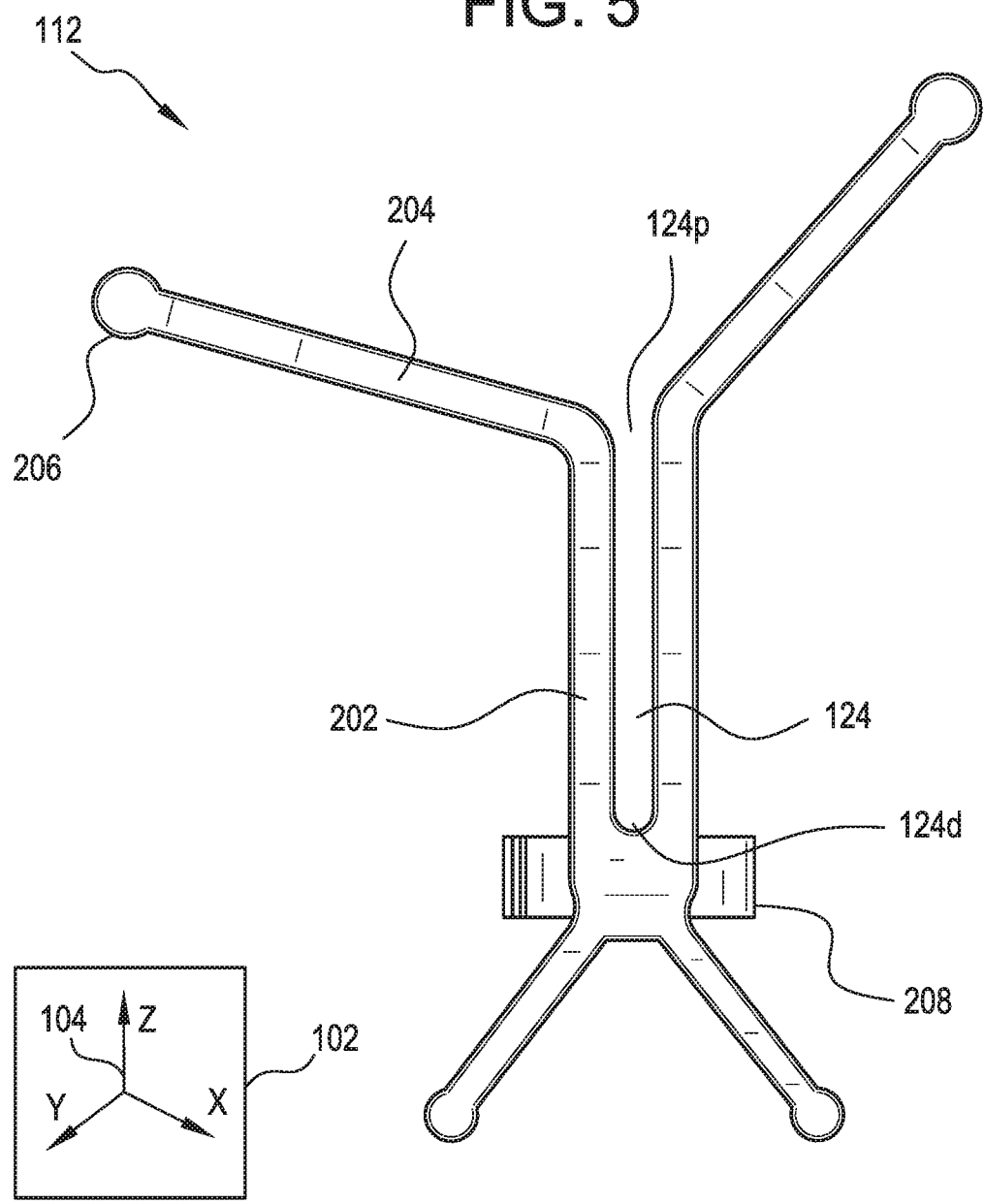
FIG. 5 is a front view of a main array of the navigated instrument guide system shown in FIG. 1.
Figure 6:
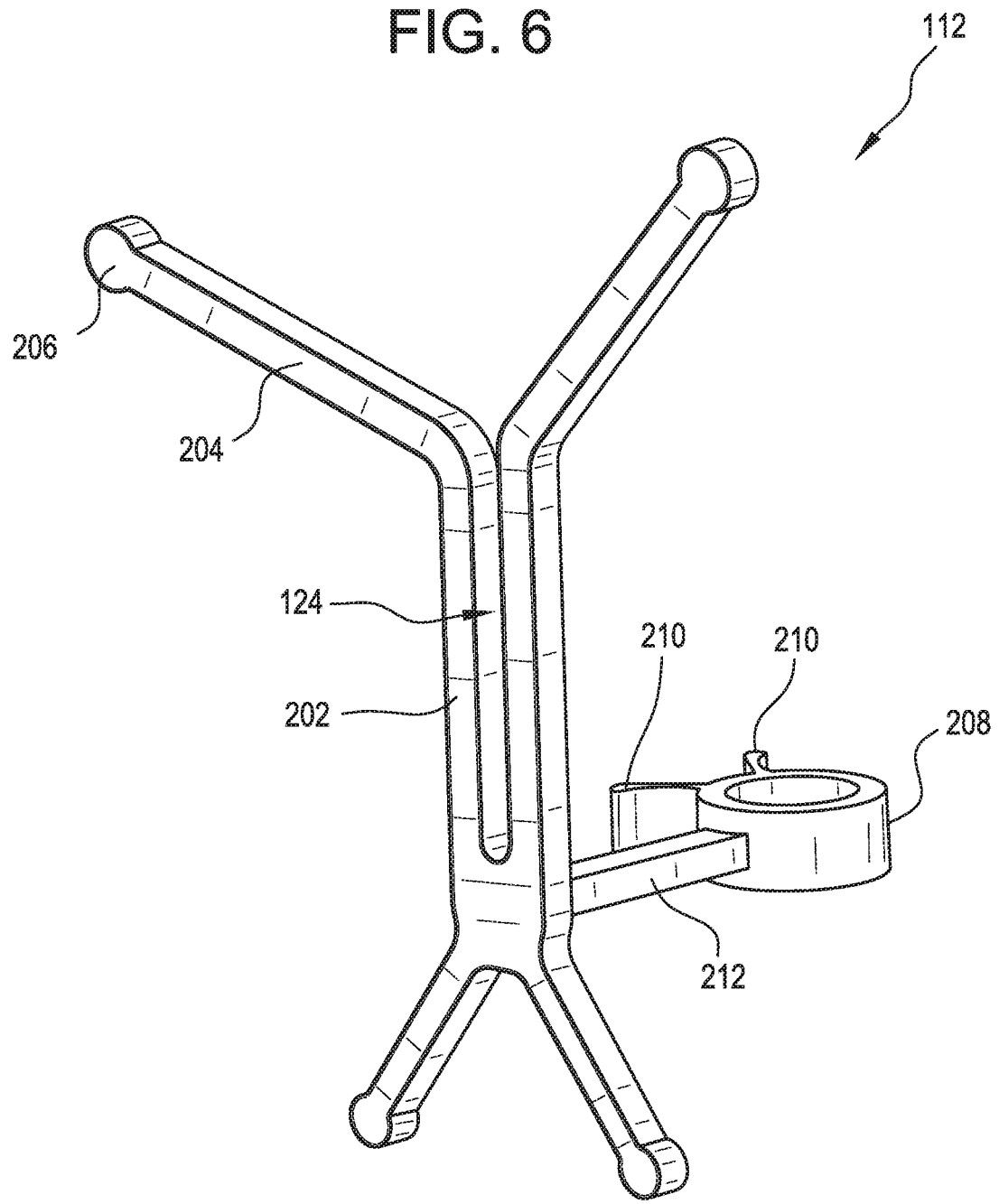
FIG. 6 is a perspective view of the main array of FIG. 5.

Components of the navigated instrument system 101 will now be described with reference to FIGS. 5-9. The main array 112 is shown in FIGS. 5 and 6. As introduced above, the main array 112 can be coupled to, and configured to locate a position of, the robotic arm 120. In this manner, positional information from the one or more markers of the main array 112 can be used to identify a position of the robotic arm 120 in three-dimensional space. As the main array 112 can be coupled to the robotic arm 120, the main array can be first in a chain of potential positioning errors with respect to the robotic arm 120 and components associated therewith. Accordingly, the main array 112 can be a large array, i.e., larger in size than the mounted array 114, which can improve accuracy and precision of positioning information obtained from the main array. Sizing of the main array 112, however, can be balanced with maneuverability of the main array within the surgical space and operating room such that the main array does not get in the way of a surgeon, nurse, and/or robotic components, and can be placed such that the navigation camera 125 can capture views of the main array without tilt or distortion.

The main array 112 can include a frame 202 having one or more branches 204. The slot 124 can be formed by the frame 202. The slot 124 can extend from a proximal end 124*p* to a distal end 124*d* along a longitudinal axis of the main array 112, and can be configured to receive the mounted array 114 such that the mounted array can translate longitudinally within the slot 124. Each branch 204 of the main array 112 can have an attachment feature 206 that can receive a sphere-shaped fiducial or other marker 113 for use with a navigation system. The attachment feature(s) 206 can be arranged in predetermined positions and orientations with respect to one another and/or the frame 202. The attachment features 206 can be positioned such that, in use, the one or more markers 113 attached thereto can be placed within a field of view of a navigation system and can be identified in images captured by the navigation system (e.g., by navigation system camera 124). By way of non-limiting example, the one or more markers 113 can include infrared reflectors, LEDs, and so forth. The branches 204 and/or attachment features 206 can be arranged on the main array 112 with different positions and/or orientations to that of the illustrated main array. For example, while the main array 112 has four branches 204 with each branch having a single attachment feature 206, a main array can have a greater or fewer number of branches and/or attachment features. The main array 112 design, including number, positioning, and orientation of branches 204 and/or markers 206, can take into account factors such as manufacturing constraints and cost, array stability, array weight, etc. The main array 112 can include an inertial measurement unit (IMU), an accelerometer, a gyroscope, a magnetometer, other sensors, or combinations thereof. In some embodiments, the sensors can transmit position and/or orientation information to a navigation system, e.g., to a processing unit of the navigation system and/or a processing unit of a robotic surgical system. The one or more markers 113 of the main array 112 can convey positional information in all degrees of freedom (i.e., along the x-, y-, and z-axis of the coordinate system 102) of the component(s) to which the main array is coupled or to which there is a known positional relationship. In other words, positional information captured from the one or more markers 113 of the main array by the navigation system can identify a position of the distal end of the robotic arm 120 and/or the instrument mount 116 in the x-, y-, and z-directions.

The main array 112 can include a coupling ring 208 that can be configured to securely couple the main array 112 to the robotic arm 120 in a known and precise position and orientation. In some embodiments, the coupling ring 208 can clamp or otherwise couple the main array 112 to the instrument mount 116 which, in turn, can be securely coupled to the robotic arm 120. In other embodiments, the main array 112 can be directly mounted along the robotic arm 120. The coupling ring 208 can include a release mechanism, for example tabs 210, that can be actuated by a robotic and/or human user and can release the clamping force or other coupling mechanism of the coupling ring 208. Additional details of non-limiting embodiments of the coupling ring 208 can be found in U.S. Patent Application Publication No. 2018/0344301, filed on May 31, 2017, and entitled "Coupling Devices for Surgical Instruments and Related Methods" to Wehrli et al., which is hereby incorporated by reference in its entirety. In some embodiments, the coupling ring 208 can be formed integrally with the main array 112. For example, a post 212 can extend from a back-facing side of the main array 112 to the coupling ring 208. In other embodiments, the main array 112 can be attached to the coupling ring 208 by way of a secure coupling assembly, such as, for example, the coupling assemblies disclosed in U.S. patent application Ser. No. 16/696,126, filed on Nov. 26, 2019, and entitled "Instrument Coupling Interfaces and Related Methods" to Philippe Lindenmann et al. and subject to common ownership and assignment to the present application, which is hereby incorporated by reference in its entirety.

Figure 7:
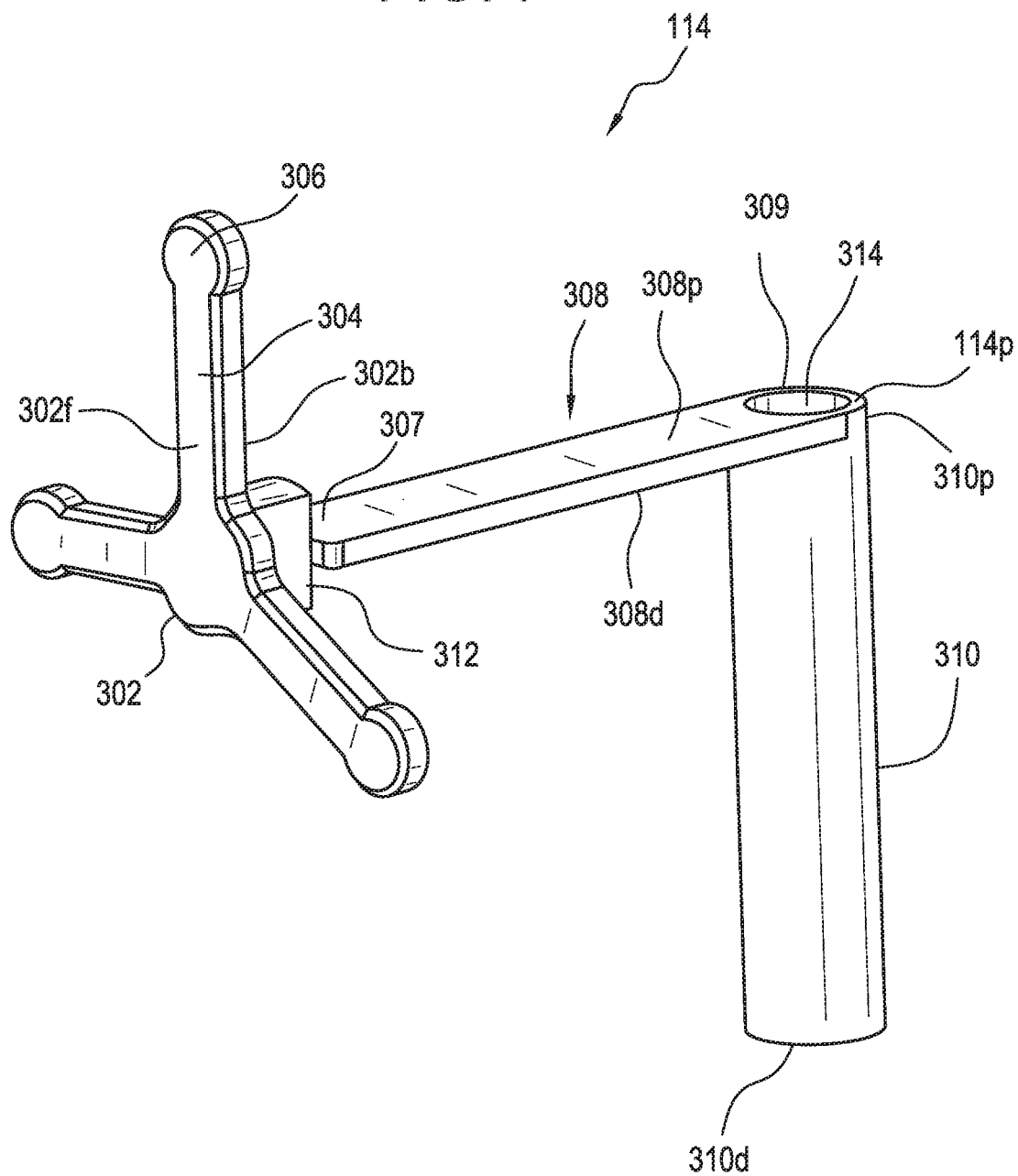
FIG. 7 is a perspective view of a mounted array of the navigated instrument guide system shown in FIG. 1.

FIG. 7 shows a perspective view of the mounted array 114. As described above, the mounted array 114 can be configured to identify and track the depth position of an instrument (e.g., the instrument 130) received within the navigated instrument system 101 of the robotic arm 120. The mounted array 114 can include an array frame 302 having one or more branches 304. Each branch 304 of the mounted array 114 can have an attachment feature 306 that can receive a sphere-shaped fiducial or other marker 115, as described above with respect to the main array 112. The fiducial(s) or other marker(s) 115 of the mounted array 114 can function in the manner as described above with respect to the main array 112. Accordingly, for sake of brevity, description of such function is omitted here. As described in further detail below, the mounted array frame 302 can be smaller, and, in some cases, significantly smaller, than the mounted array frame 202 such that the mounted array frame 302 and any associated fiducial(s)/marker(s) 115 can be wholly received within a footprint or a perimeter defined by the markers 113 of the main array 112.

An extension 308 can extend from the frame 302 to a tubular body 310 of the mounted array 114. In some embodiments, a connecting portion 312 can extend between the frame 302 and the extension 308. More particularly, the connecting portion 312 can extend from a back-facing side 302b of the frame 302, where the back-facing side of the frame is opposite a front-facing side 302f. The connecting portion 312 can be configured to be received within the slot 124 of the main array 112. To that end, the connecting portion 312 can have a size and dimensions complementary to that of the slot 124 such that the connecting portion can translate longitudinally within the slot 124. In some embodiments, the connecting portion 312 can have a generally rectangular cross-section to match a cross-section of the slot 124. Other geometries of the connecting portion 312 and the slot 124 can be within the scope of the present disclosure, so long as the connecting portion 312 can be received within the slot 124 and can allow the mounted array 114 to translate along a longitudinal axis of the slot relative to the main array 112. The extension member 308 can extend from a first end 307 at the connecting portion 312 to a second end 309 at the tubular body 310. The extension can have a proximal facing surface 308p and a distal facing surface 308d. The proximal end 114p of the mounted array 114 can be defined by the proximal facing surface 308p of the extension 308 at the second end 309, which can form an outer circumference face of a proximal end 310p of the tubular body 310.

The tubular body 310 can have a lumen 314 that extends from the proximal end 310p of the tubular body to a distal end 310d of the tubular body. The lumen 314 can be configured to receive an instrument (e.g., instrument 130) when the instrument is inserted and received within the instrument mount 116. As described in detail below, the tubular body 310 can be configured to be slidably received within the instrument mount 116. More particularly, the distal end 310d of the tubular body 310 can be received within the lumen of the instrument mount 116. The tubular body 310 can be configured to translate along the longitudinal axis of the lumen with respect to the instrument mount 116. The second end 309 of the extension can form a stop such that the tubular body 310 cannot translate distally within the lumen of the instrument mount 116 beyond the proximal end 310p of the tubular body. The distal-facing surface 308d of the second end 309 of the extension 308 can abut a proximal facing surface of the instrument mount 116 and can prevent distal translation of the tubular body 310. The distal facing surface 308d of the second end 309 of the extension 308 can also serve as a proximal contact point for the biasing element 126.

The instrument mount 116 will now be described with respect to FIGS. 8 and 9, which show an assembled view and an exploded view of the instrument mount, respectively. The instrument mount 116 can be attached to the robotic arm 120 and can be configured to receive an instrument 130 and the tubular body 310 of the mounted array 114 therein. Over the course of a surgical procedure, a plurality of instruments can be received within the instrument mount 116. For example, during a single surgical procedure, a first instrument can be inserted into the instrument mount 116, the first instrument can later be removed, and a second instrument can be inserted into the instrument mount. As discussed above, the instrument mount 116 can include the instrument guide 117 received within a lumen of the adapter 119. More particularly, the adapter 119 can be a tubular body having a proximal end 119p and a distal end 119d with a lumen 402 extending therebetween. The proximal end 119p can be configured to couple to the main array 112 in a known, secure, and precise manner. The proximal end 119p can be formed with one or more outer surface features that are complementary to features of the coupling ring 208 of the main array 112. In some embodiments, the proximal end 119p can include a flange 404. A proximal-facing surface 404p of the flange 404 can be configured to abut a distal-facing surface of the coupling ring 208. Such a construction can help ensure that the main array 112 can be coupled to the robotic arm 120, by way of the instrument mount 116, in the intended known position. The lumen 402 of the adapter 119 can be configured to receive the instrument guide 117 therein.

The instrument guide 117 can be a tubular body having a proximal end 117p and a distal end 117d with a lumen 406 extending therebetween. In some cases, the instrument guide 117 can be configured for use with a particular instrument, and can be swapped out during the course of a surgical procedure for another instrument guide in accordance with the particular instrument in use. For example, a particular instrument guide 117 can be selected based on an inner diameter of the lumen 406 such that the lumen 406 can accommodate an outer diameter of an instrument to be used in a surgical procedure. The lumen 406 can be configured to receive the tubular body 310 of the mounted array 114 and the instrument 130. The proximal end 117p of the instrument guide 117 can include a flange 408. A proximal-facing surface 408p of the flange 408 can serve as a stop for the distal end 126d of the biasing element 126. The flange 408 can include features, such as ridges 410, that can facilitate gripping or other manipulation (e.g., rotating or turning) of the instrument guide 117 by a user. An expanded portion 412 of the instrument guide 117 can be configured to form a friction fit between the instrument guide 117 and the adapter 119 when the expanded portion 412 is received within the lumen 402 of the adapter 119. The friction fit can secure a coupling of the instrument guide 117 with the adapter 119. In this manner, the instrument 130 and the mounted array 114 can be received within the lumen 406 of the instrument guide 117 in a known orientation. In some embodiments, the expanded portion 412 can include external threads that can be complementary to internal threads formed on an inner surface of the proximal portion 119p of the adapter 119. The external threads of the expanded portion 412 can engage with the internal threads of the proximal portion 119p of the adapter 119 to form a threaded connection between the instrument guide 117 and the adapter. In some embodiments, the distal end 117d of the instrument guide can be tapered. The tapered distal end 117d can improve ease with which the instrument guide 117 can be inserted and passed through the lumen 404 of the adapter 119, and can aide with dilation of soft tissue upon insertion of the distal end 117d of the instrument guide 117 into a patient.

Figure 10:
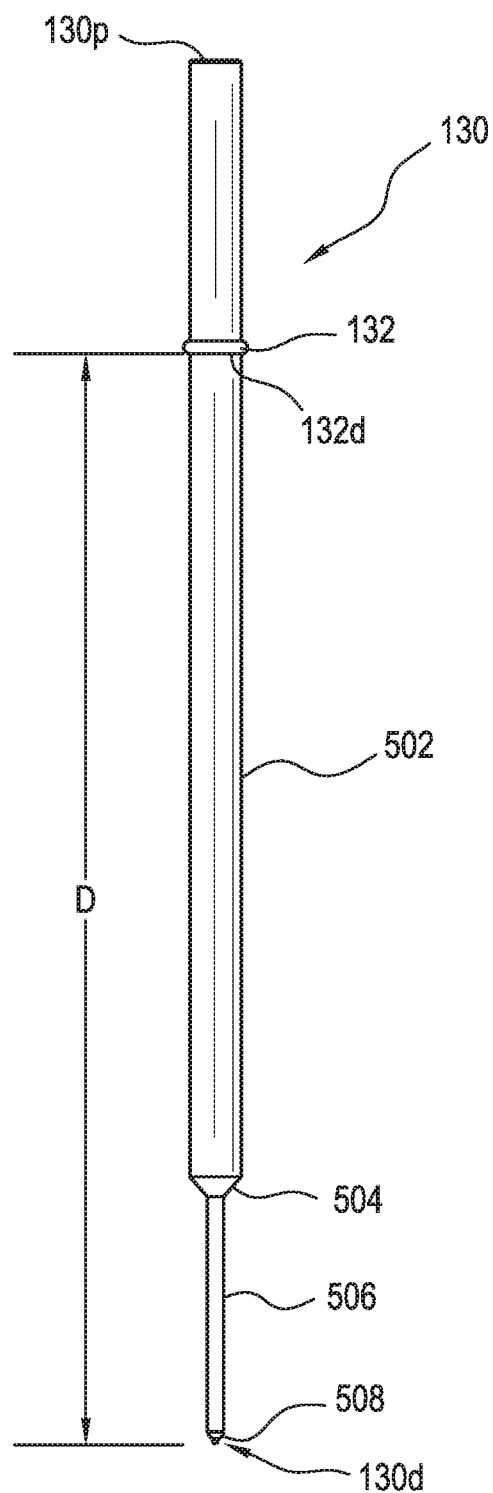
FIG. 10 is a front view of one embodiment of an instrument that can be used in association with navigated instrument guide systems of the present disclosure.

FIG. 10 illustrates one embodiment of an instrument that can be used with the navigated instrument systems of the present disclosure. In some embodiments, the instrument 130 can be a drill. The instrument 130 can have a generally tubular body 502 with a tapered portion 504 that transitions from the tubular body 502 to a drill bit 506. A drive feature 508 can be located at the distal end 130d of the instrument 130. The collar 132 can be integrally formed on the tubular body 502. The collar 132 can extend radially from the tubular body 502 and can be sized such that the collar can abut the proximal end 114p of the mounted array. In some embodiments, the collar 132 can be manufactured separately from the instrument 130 and securely and precisely attached thereto, while in other embodiments the collar 132 can be integrally formed with the instrument 130. The collar 132 can be positioned a fixed distance D from the distal end 130d of the instrument. More particularly, the fixed distance D can be measured from a distal-facing surface 132d of the collar 132 to a distal-facing surface of the distal end 130d of the instrument 130. In the embodiment shown in FIG. 10, the distal-facing surface of the distal end 130d of the instrument 130 can be a distal-facing surface of the drive feature 508. The distance D between the collar 132 and the distal end 130d of the instrument 130 can be substantially equal to the distance C between the proximal end 114p of the mounted array 114 and the distal tip 116d of the instrument mount 116, as described above. In embodiments in which a setback or buffer is employed, the distance C can be substantially equal to the distance D plus the setback or buffer distance. The instrument 130 can be manufactured such that the distance D from the collar 132 to the distal end 130d of the instrument can be precisely and accurately known. In some embodiments, the instrument 130 can be manufactured such that the distance D can be precisely and accurately known to sub-tenths of a millimeter. Precision and accuracy of the known distance D can be critical to the precision and accuracy of identifying the depth position of the distal tip 130d of the instrument 130 by the mounted array 114. While description of the instrument 130 provided herein makes reference to the drill shown in the figures, the present disclosure is also contemplated for use with other surgical tools or instruments configured to be received within the instrument mount 116, such as, for example, any of a tap, driver, needle, stylus, probe, etc.

Figure 11:
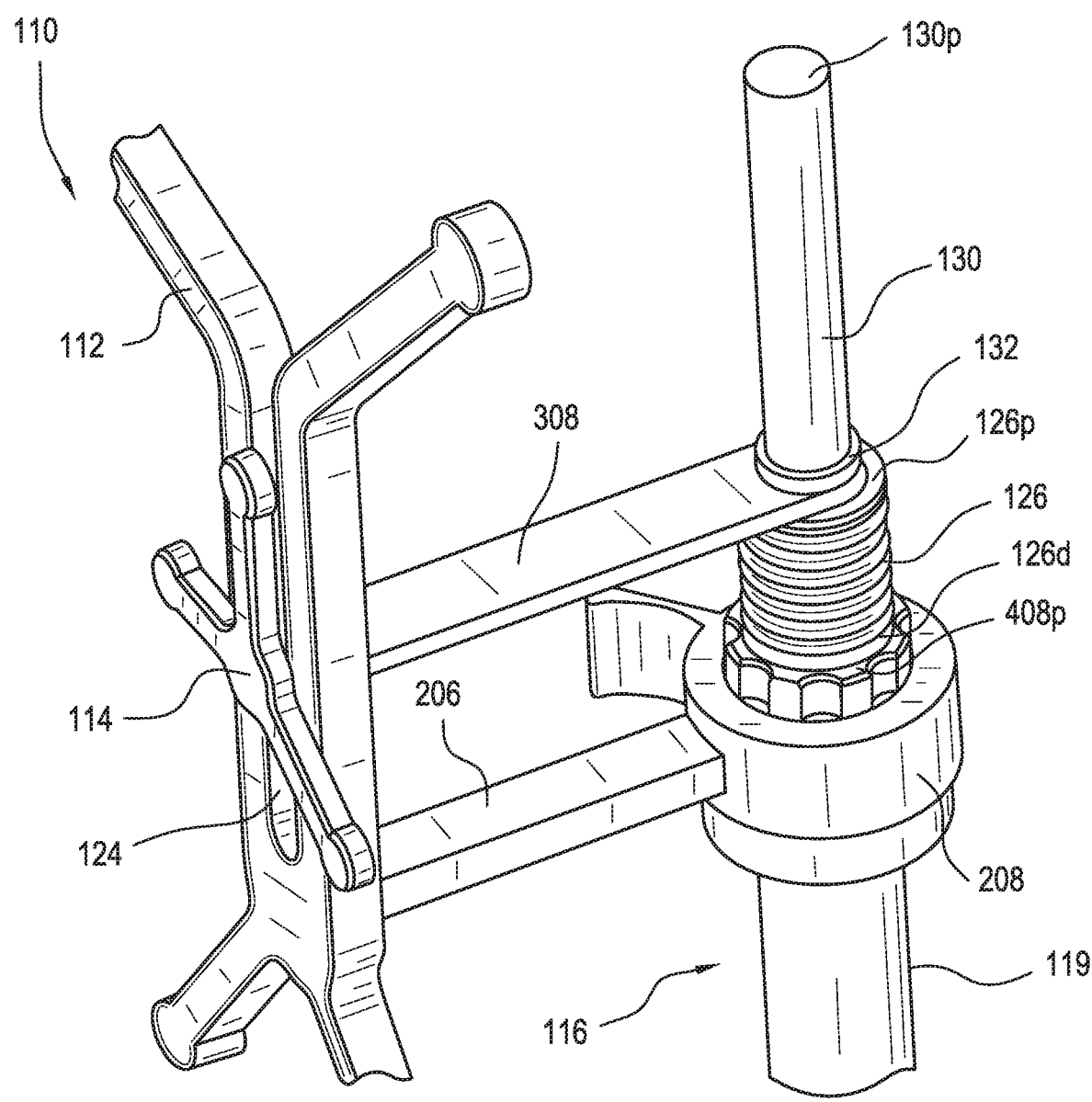
FIG. 11 is a detailed perspective view of the navigated instrument guide system of FIG. 1 with an instrument received therein.
Figure 12:
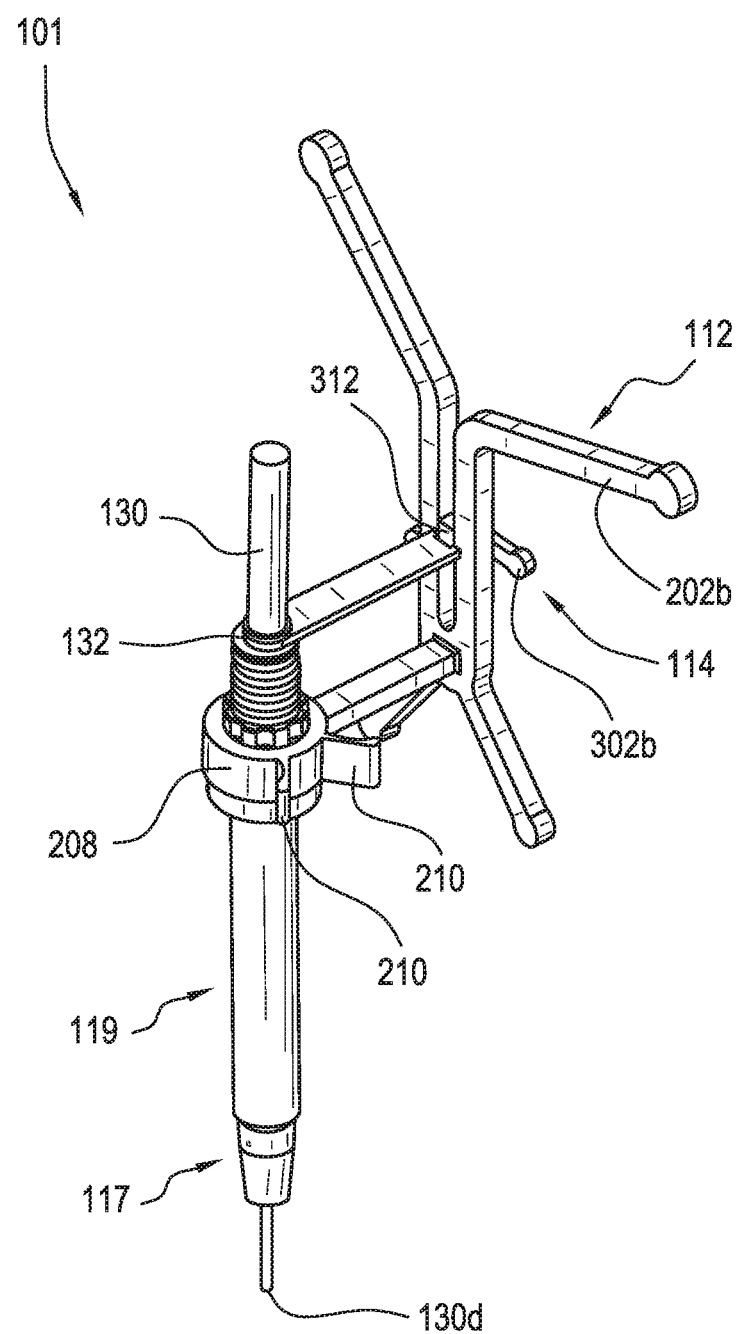
FIG. 12 is another perspective view of the navigated instrument guide system shown in FIG. 1 with an instrument received therein.
Figure 13:
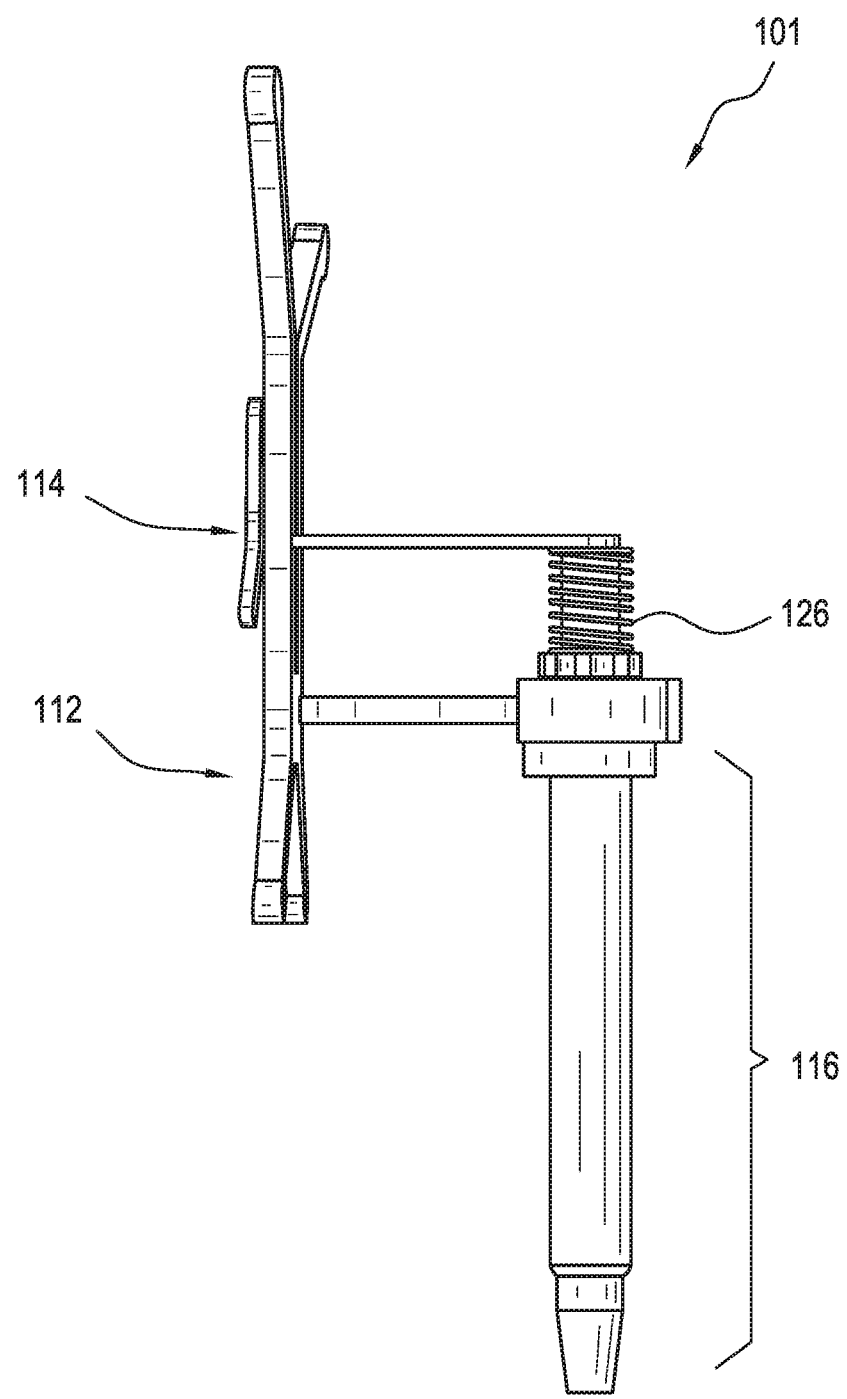
FIG. 13 is a side view of the navigated instrument guide system shown in FIG. 1.

With the components of the navigated instrument system 101 now described, FIGS. 11-13 show additional view of the navigated instrument system. FIG. 11 illustrates a partial perspective view of the navigated instrument system 101 and instrument 130, and, more specifically, shows the assembly and configuration of the navigation array unit 110 and a proximal end of the instrument mount 116 with the mounted array 114 dragged distally by the instrument 130. FIG. 12 shows another perspective view of a back side of the navigated instrument system 101 with the instrument 130. FIG. 13 shows the navigated instrument system 101 from a side view.

As shown in FIGS. 11-13, the mounted array 114 can be located wholly within a perimeter or footprint of the main array 112. In other words, the one or more markers 115 of the mounted array 114 can be located within a perimeter formed by the one or more markers 113 of the main array 112 at all times. Such an arrangement can serve to greatly reduce the risk that a navigation system crosses signals between a marker 113 of the main array 112 and a marker 115 of the navigated array 114. An optical navigation system can mix up markers, especially as one marker passes by or in near proximity to another marker and can mis-identify which array a particular marker is associated with. The navigation array unit 110 of the present disclosure can substantially reduce a risk of improper navigation marker association by isolating the markers 113 of the main array 112 from the markers 115 of the mounted array 114, even as the markers 115 can move relative to the main array 112. As shown, the mounted array 114 can include three markers 115. Each of these three markers 115 can maintain a constant distance and position relative to one another and the mounted array 114. With such a three-star array, a navigation system can clearly identify the markers 115 as associated with the mounted array 114 and, accordingly, a z-axis or depth axis of the instrument 130. Misidentification of a marker 115 by the navigation system can be significantly reduced in an array with three markers as compared to arrays having fewer than three markers. In other embodiments, the mounted array 114 can have a greater or fewer number of markers 115.

Figure 14:
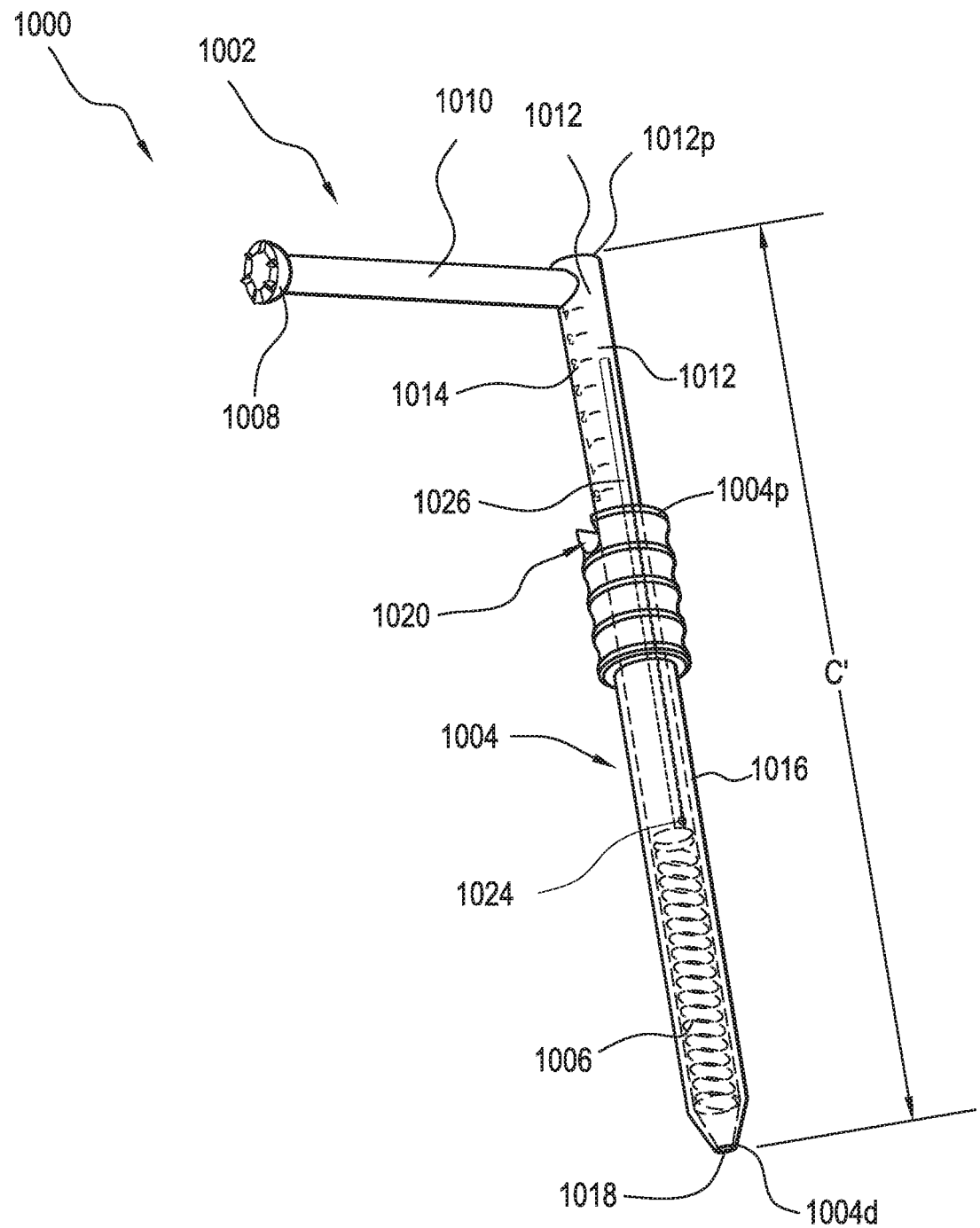
FIG. 14 shows another embodiment of a navigated instrument guide system according to the present disclosure.
Figure 15:
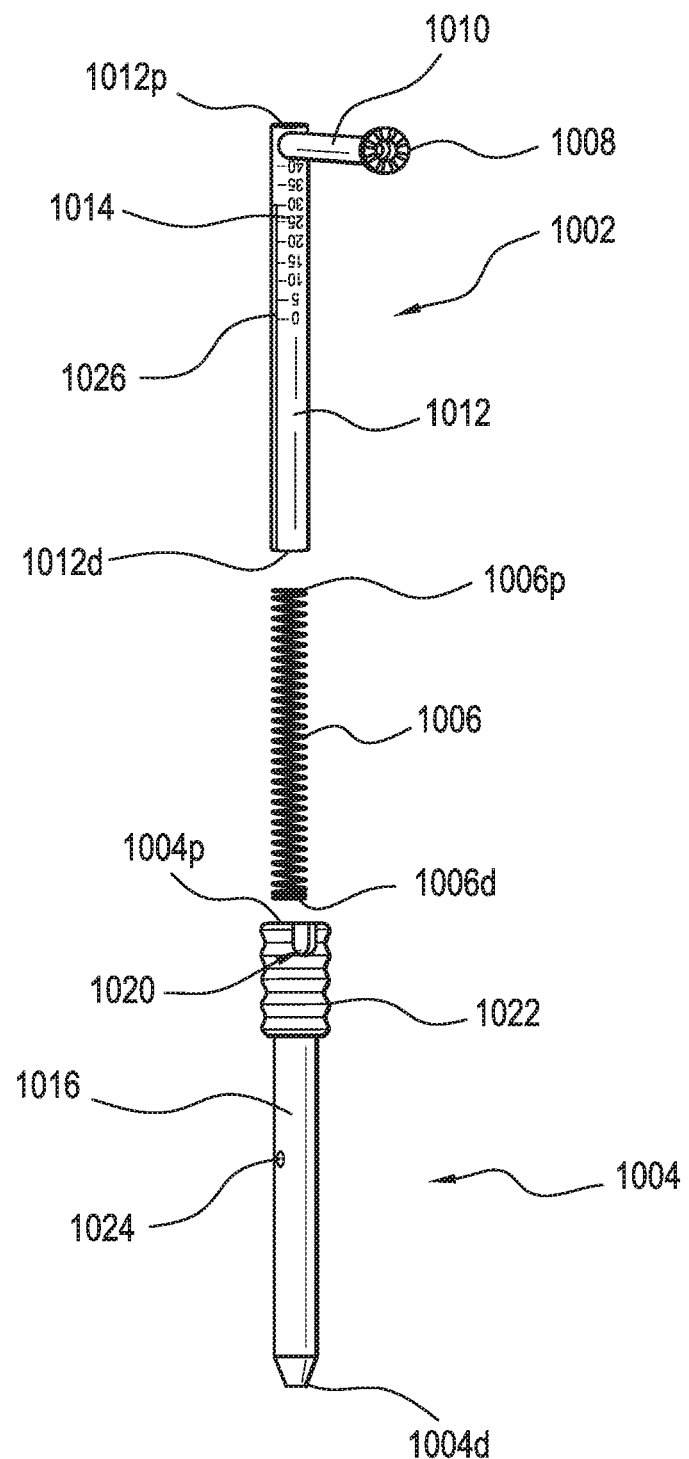
FIG. 15 shows an exploded view of the navigated instrument guide system of FIG. 14.

An alternative embodiment of a navigated instrument system 1000 in accordance with the present disclosure is illustrated in FIGS. 14 and 15. The navigated instrument system 1000 is shown in an assembled configuration in FIG. 14 and in an exploded view in FIG. 15. Except as indicated below, the structure, operation, and use of this embodiment is similar or identical to that of the navigated instrument system 101 described above. Accordingly, a detailed description of said structure, operation, and use is omitted here for the sake of brevity. The navigated instrument system 1000 can include a mounted array 1002, an instrument mount 1004, and a biasing element 1006 placed within the instrument mount. As with the navigated instrument system 101, described above, the instrument mount 1004 can be configured to securely attach to a distal end of a robotic arm (not shown). By way of non-limiting example, the instrument mount 1004 can be securely attached or coupled to the robotic arm with an adapter, such as the adapter 119 shown in FIG. 3B. Further, as described above, a main array (not shown) can be securely attached to the instrument mount 1004 and can be configured to identify a position of the robotic arm and the end effector 1000. The mounted array 1002 can be received within a slot of the main array and can be configured to translate longitudinally along the slot with longitudinal translation of an instrument received within the instrument mount 1004. Accordingly, the mounted array 1002 can be configured to determine a depth position of the instrument received within the instrument mount 1004 in a manner similar to that described above.

The mounted array 1002 can include an array frame (not shown), a connecting member 1008, an extension member 1010, and a tubular body 1012. The connecting member 1008 can extend from the array frame and can be configured to translate longitudinally within a slot of the main array. The tubular body 1012 can have a proximal end 1012p and a distal end 1012d with a lumen extending through the tubular body. The lumen of the tubular body 1012 can be configured to receive an instrument (e.g., the instrument 130), as described above with respect to the navigated instrument system 101. At least a portion of the tubular body 1012 can be received within a lumen of the instrument mount 1004. More particularly, the distal end 1012d of the tubular body can be received within a lumen of the instrument mount such that the tubular body 1012 can translate along a longitudinal axis of the instrument mount. As described above, a collar of the instrument received within the lumen of the mounted array 1002 can be configured to distally drag the mounted array relative to the instrument mount 1004 and the main array.

In some embodiments, the biasing element 1006 can abut the distal end 1012d of the tubular body 1012. The biasing element 1006 can bias the tubular body 1012 towards a proximal end 1006p of the instrument mount 1006. The biasing element 1006 can impart a desired drag force that can semi-rigidly maintain a position of the mounted array 1002 in a proximally biased position relative to the instrument mount 1004 and a main array, while continuing to permit longitudinal movement of the mounted array if, for example a user (i.e., a robot or a human) overcomes the drag force with distal translation of an instrument (e.g., the instrument 130) when a collar of the instrument contacts the proximal portion 1012p of the mounted array.

Similar to the previously described embodiment, a distance C' between a proximal facing surface of the proximal end 1012p of the tubular body 1012 and the distal end 1116d of the instrument mount 1116 can be known to an accurate and precise measurement. Moreover, in some embodiments, the distance C' and the distance D between the collar of the instrument and the distal tip of the instrument, as described above with reference to FIG. 10, can be substantially equal. Accordingly, as described above, the mounted array 1002 can translate a known distance (i.e., a distance tracked by marker(s) of the mounted array) with application of a distal drag force from the collar of the instrument as the instrument translates distally within the instrument mount 1004. The one or more trackers of the mounted array 1002 can be used to track and measure the distance that the mounted array translates distally. The tracked distance traveled by the mounted array 1002 can be used to identify a depth position of the distal tip of the instrument. In some embodiments, the tubular body 1012 can also include one or more visual depth indicators 1014 along an outer surface of the tubular body such that a user can visually confirm or estimate the distance the mounted array 1002 translates within the lumen of the instrument mount 1004.

The instrument mount 1004 can have a generally tubular body 1016 with the lumen of the instrument mount extending from the proximal end 1004p to the distal end 1004d of the tubular body. The lumen of the instrument mount 1004 can extend through the distal end 1004d of the instrument mount at a distal opening 1018. In some embodiments, the distal end 1004d of the tubular body 1012 can taper to the distal opening 1018. As discussed above, the tubular body 1012 of the mounted array 1002 can be inserted into a proximal end of the lumen of the instrument mount 1004. A stop feature 1020 can be formed at the proximal end 1004p of the instrument mount 1004. A geometry of the stop feature 1020 (i.e., a cross-section of the stop feature) can be complementary to a geometry of the extension 1010 of the mounted array 1002. The stop feature 1020 can be configured to receive the extension 1010 as the tubular body 1012 moves distally within the lumen of the instrument mount 1004. Accordingly, distal movement of the mounted array 1002 can be prevented when the extension 1010 is fully received within the stop feature 1020. One or more grip enhancing features 1022 can be formed on an outer surface of the proximal portion 1004p of the instrument mount 1004. In some embodiments, the grip enhancing features 1022 can secure a coupling between the main array (not shown) and the instrument mount 1004. By way of non-limiting example, the grip enhancing features 1022 can include one or more bellows formed on the outer surface of the instrument mount 1004, which can engage with complementary features of a coupling ring of the main array.

Alignment of the instrument mount 1004 and the mounted array 1002 can be maintained with one or more alignment features. More particularly, the instrument mount 1004 can have one or more alignment holes 1024 that can extend through the tubular body of the instrument mount. Each of the one or more alignment holes 1024 of the instrument mount 1004 can align with an alignment groove 1026 of the tubular body 1012 of the mounted array 1002. Each alignment groove 1026 can extend longitudinally along at least a portion of the tubular body 1012. In some embodiments, the alignment groove 1026 can extend from an outer surface of the tubular body 1012 towards the lumen of the tubular body without extending into the inner lumen. An alignment member (not shown), for example, a pin, can be inserted through the alignment hole 1024 and into the alignment groove 1026. In this manner, rotation of the tubular body 1012 relative to the instrument mount 1004 can be prevented. The alignment member can also serve to capture the biasing element 1006 and prevent its inadvertent removal from the instrument mount 1016 if, for example the tubular body 1012 is removed during a procedure. While a single alignment hole 1024 and alignment groove 1026 are illustrated in FIGS. 14 and 15, additional alignment holes and grooves may be formed in instrument mount 1004 and tubular body 1012 of the mounted array 1002, respectively. Maintaining a known and precise alignment between the instrument mount 1004 and the tubular body 1012 of the mounted array 1002 can aide in conveying accurate and precise location information from markers of the mounted array 1002 to the robotic system or the navigation system.

Although specific embodiments are described above, changes may be made within the spirit and scope of the concepts described. For example, the navigation array unit 110 can include two or more mounted arrays 114 such that a depth or advancement of two or more instruments 130 can be monitored. In some such embodiments, the main array 112 can have two or more slots 124, such that each mounted array 114 can travel along a respective slot 124. In other embodiments, the two or more mounted arrays 114 can be received within and travel along a single slot 124 but can be placed such that the two or more mounted arrays 114 do not come into contact with one another. Accordingly, it is intended that this disclosure not be limited to the described embodiments, but that it have the full scope defined by the language of the claims. The above embodiments describe coupling a navigation array to an instrument or an instrument adapter. While this is one contemplated use, the methods and devices of the present disclosure can be equally adapted for use with other objects. As such, the devices and components described herein can be formed in a variety of sizes and materials appropriate for use in various applications. All publications and references cited herein are expressly incorporated herein by reference in their entirety.

The invention claimed is:

1. A surgical assembly comprising:
a first array coupled to a surgical robot arm and configured to locate a position of a distal portion of the arm;
an instrument mount coupled to the robot arm, the instrument mount having a proximal end, a distal end, and a lumen extending therebetween; and
a second array configured to move relative to the instrument mount and the first array as an instrument is passed through the lumen of the instrument mount;
wherein the second array is configured to move along a slot defined by the first array.

2. The assembly of claim 1, wherein the first array configured to locate the position of the distal portion of the arm is configured to locate a position of a longitudinal axis of the instrument mount.

3. The assembly of claim 1, wherein the second array is configured to translate along a longitudinal axis of the instrument mount.

4. The assembly of claim 1, wherein the first array is stationary relative to a distal portion of the robot arm and the second array is configured to move longitudinally relative to the first array and the instrument mount with longitudinal movement of an instrument received within the lumen of the instrument mount.

5. The assembly of claim 1, wherein the second array includes an array frame, an extension, and a tubular body, the tubular body having a proximal end, a distal end, and a lumen extending therebetween, wherein the lumen is configured to receive an instrument therethrough.

6. The assembly of claim 5, wherein the lumen of the second array is coaxial with the lumen of the instrument mount.

7. The assembly of claim 1, further comprising a biasing element configured to urge the second array proximally relative to the instrument mount.

8. The assembly of claim 7, wherein the biasing element is disposed within an inner lumen of the instrument mount.

9. The assembly of claim 7, wherein the biasing element is disposed proximal to the instrument mount.

10. The assembly of claim 1, wherein the second array includes a plurality of tracking elements.

11. The assembly of claim 10, wherein the first array includes a greater number of tracking elements than the second array.

12. A surgical robot system comprising:
an instrument mount coupled to a surgical robot arm, the instrument mount having a proximal end, a distal end, and a lumen extending therebetween;
an instrument having an instrument body and a collar formed on the instrument body at a location proximal to a distal tip of the instrument;
a first array component configured to locate a position of a distal portion of the surgical robot arm;
a second array component having a tubular body received within the lumen of the instrument mount, wherein the second array component is configured to advance distally with the instrument when the collar of the instrument contacts a proximal portion of the second array component; and
a biasing element configured to urge the second array proximally relative to the instrument mount.

13. The system of claim 12, wherein the biasing element is a spring extending between the second array component and the instrument mount such that the spring compresses and expands with longitudinal movement of the second array component.

14. The system of claim 13, wherein the spring is biased away from the instrument mount.

15. The system of claim 12, wherein the instrument is any of a drill, tap, needle, stylus, and probe.

16. The system of claim 12, wherein a distance between a proximal end of the second array component and a distal end of the instrument mount is substantially equal to a distance between the collar formed on the instrument body and the distal tip of the instrument.

17. The system of claim 12, wherein the second array is configured to move along a slot defined by the first array.

18. A surgical assembly comprising:
a surgical robot arm;
an instrument operably connected to the arm such that the instrument moves longitudinally with respect to the arm;
a first array attached to the arm to indicate a position of the arm; and
a second array engaging the instrument and slidably disposed in the first array, wherein the second array is configured to move along a slot defined by the first array, and wherein the second array indicates a depth of the instrument with respect to the position of the arm.

19. The surgical assembly of claim 18, wherein the arm further comprises an instrument mount, and the first array is attached to the instrument mount.

20. The surgical assembly of claim 19, wherein the instrument mount defines a lumen, and the second array has a tubular body disposed within the lumen.

21. The surgical assembly of claim 19, further comprising a biasing element configured to urge the second array proximally relative to the instrument mount.

22. The surgical assembly of claim 18, wherein the second array engages a collar of the instrument as the instrument moves longitudinally with respect to the arm such that the second array moves with the instrument.

* * * * *